US008816096B2

(12) United States Patent
Korte et al.

(10) Patent No.: US 8,816,096 B2
(45) Date of Patent: *Aug. 26, 2014

(54) PROCESS FOR PREPARING SUBSTITUTED N-PHENYLHYDROXYLAMINES

(75) Inventors: Alexander Korte, Sao Paulo (BR); Michael Puhl, Hirschberg (DE); Tao Qu, Ludwigshafen (DE); Marco Coppola, Goellheim (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/003,387

(22) PCT Filed: Mar. 7, 2012

(86) PCT No.: PCT/EP2012/053878
§ 371 (c)(1),
(2), (4) Date: Sep. 5, 2013

(87) PCT Pub. No.: WO2012/120029
PCT Pub. Date: Sep. 13, 2012

(65) Prior Publication Data
US 2013/0338373 A1    Dec. 19, 2013

(30) Foreign Application Priority Data
Mar. 9, 2011    (EP) .................... 11157524

(51) Int. Cl.
*C07D 231/22*    (2006.01)
(52) U.S. Cl.
USPC ...................................... 548/371.1
(58) Field of Classification Search
CPC ........................................ C07D 231/22
USPC ..................................... 548/371.1
See application file for complete search history.

(56) References Cited

U.S. PATENT DOCUMENTS

| 4,299,778 A | 11/1981 | Pilgram |
| 5,824,705 A | 10/1998 | Mueller et al. |
| 5,831,093 A | 11/1998 | Götz et al. |
| 5,869,517 A | 2/1999 | Müller et al. |
| 6,255,489 B1 | 7/2001 | Klintz et al. |
| 8,563,748 B2 * | 10/2013 | Korte et al. ............... 548/371.1 |

FOREIGN PATENT DOCUMENTS

| EP | 0212375 | 3/1987 |
| WO | WO 9315046 | 8/1993 |
| WO | WO 9601256 | 1/1996 |
| WO | WO 9622967 | 8/1996 |
| WO | WO 9912911 | 3/1999 |
| WO | WO 2012120029 | 9/2012 |

OTHER PUBLICATIONS

Ayyangar et al., "Facile Transfer-Reduction of Nitroarenes to N-arylhydroxylamines with Hydrazine in the Presence of Raney Nickel," Synthesis, vol. 11, (1984), pp. 938-941, 1162.
Entwistle et al., "Rapid Catalytic Transfer Reduction of Aromatic Nitro Compounds to Hydroxylamines," Tetrahedron, vol. 34, No. 2, (1978), pp. 213-215.
Fabio et al., "Synthesis and Pharmacological Characterization of a Conformationally Restrained Series of Indole-2-Carboxylates as in vivo Potent Glycine Antagonists," Farmaco, Society Chimica Italiana, vol. 56, (2001), pp. 791-798.
International Preliminary Report on Patentability, issued in PCT/EP2012/053878, dated Sep. 19, 2013.
International Search Report, issued in PCT/EP2012/053878, dated Apr. 12, 2012.
Nunna et al., "S-(n-aryl-n-hydroxycarbamoyl) Glutathione Derivatives are Tight-Binding Inhibitors of Glyoxalase I and Slow Substrates for Glyoxalase II," Journal of Medicinal Chemistry, vol. 37, No. 14, (1994), pp. 2161-2166.
Oxley et al., "N-Acetyl-N-Phenylhydroxylamine via Catalytic Transfer Hydrogenation of Nitrobenzene using Hydrazine and Rhodium on Carbon," Organic Syntheses, Coll., vol. 8, (1993), p. 16; vol. 67, (1989), p. 187.

* cited by examiner

*Primary Examiner* — Kamal Saeed
(74) *Attorney, Agent, or Firm* — Brinks Gilson & Lione

(57) ABSTRACT

The present invention relates to a process for the preparation of 2-[[[1-(4-chlorophenyl)-1H-pyrazol-3-yl]oxy]methyl]phenyl]-hydroxylamine from the correspondingly substituted nitrobenzene compound.

8 Claims, No Drawings

PROCESS FOR PREPARING SUBSTITUTED N-PHENYLHYDROXYLAMINES

This application is a National Stage application of International Application No. PCT/EP2012/053878, filed Mar. 7, 2012, the entire contents of which is hereby incorporated herein by reference. This application also claims priority under 35 U.S.C. §119 to European Patent Application No. 11157524.7, filed Mar. 9, 2011, the entire contents of which is hereby incorporated herein by reference.

The present invention relates to a process for the preparation of 2-[[[1-(4-chlorophenyl)-1H-pyrazol-3-yl]oxy]methyl]phenyl]-hydroxylamine from the correspondingly substituted nitrobenzene compound.

2-[[[1-(4-chlorophenyl)-1H-pyrazol-3-yl]oxy]methyl]phenyl]-hydroxylamine is an important precursors in one synthesis route for pyraclostrobin, the latter being a commercial important fungicide, which is disclosed, for example, in WO 93/15046 and WO 96/01256.

For the reduction of aromatic nitro compounds to N-phenylhydroxylamines several methods are available. Among those used on a technical scale reductions with metals, such as, for example zinc and amalgams have the drawback of having an adverse waste material balance, whereas, in comparison, heterogeneous hydrogenations using transition metals such as platinum or palladium as catalysts are considered favourable. In order to obtain reasonable selectivity for the N-phenylhydroxylamine these reactions have to be carried out in the presence of additives, such as sulfur compounds or organic bases, in particular amines, which partially poison or inactivate the catalyst (see for example EP 212375, WO 96/22967 and WO 99/12911). The use of these additives, however, may be accompanied by disadvantages, such as a diminished activity of the recycled catalyst after a few reaction cycles or difficulties with the removal of the additive during work-up, as removal of the additives by distillation is often not possible because of the thermal lability of the obtained N-phenlyhydroxylamines.

Alternatively the reduction can be accomplished by transfer hydrogenation using for example hydrazine or phosphinic acid as reducing agents in combination with one of the transition metals rhodium, iridium, nickel or palladium as catalyst (N. R. Ayyangar et al., Synthesis 1984, 938; I. D. Entwistle et al., Tetrahedron 1978, 34, 213 and P. W. Oxley et al., Organic Syntheses 1989, 67, 187). However, most publications dealing with the reduction of nitro benzene derivatives to the corresponding hydroxylamines by this approach describe only simple nitrobenzene derivatives as substrates. In addition, the question of selectivity has not yet been fully evaluated. However, a high selectivity is crucial in large scale synthesis.

Thus, it is the object of the present invention to provide processes for preparing 2-[[[1-(4-chlorophenyl)-1H-pyrazol-3-yl]oxy]methyl]phenyl]-hydroxylamine that are easy to perform and are suitable for industrial scale production, and which should be on the one hand have a satisfactory reaction rate combined with a high selectivity.

The object is achieved by the processes described in detail below.

The present invention relates to a A process for the preparation of a substituted N-phenylhydroxylamine of formula I

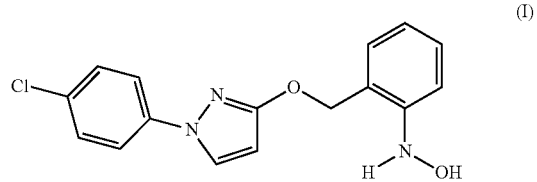 [SMILES: ONc1ccccc1COc1ccn(-c2ccc(Cl)cc2)n1]

by reduction of the correspondingly substituted nitrobenzene compound of formula II,

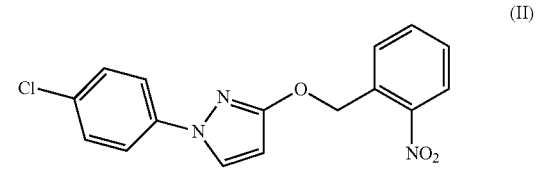 [SMILES: O=[N+]([O-])c1ccccc1COc1ccn(-c2ccc(Cl)cc2)n1]

wherein the reduction is carried out by reacting the substituted nitrobenzene compound in the presence of a rhodium catalyst either by using hydrogen or hydrazine for the reduction.

Reduction of simple nitrobenzene derivatives as substrates in the presence of a rhodium catalyst result in the formation of significant amounts of the corresponding amine. Surprisingly, reduction of the complex substituted nitrobenzenes of formula I substrates in the presence of a rhodium catalyst result resulted in a reduced formation of these by-products.

In a preferred embodiment, the reduction is carried out reacting the substituted nitrobenzene compound with hydrazine in the presence of a rhodium catalyst.

The process of the present invention is a kind of transfer hydrogenation, where the hydrazine compound acts as the reducing agent, the reaction being catalyzed by the rhodium catalyst. In other words, the hydrogen atoms of the hydrazine compound are transferred to the nitro group of the substituted nitrobenzene compound, thereby reducing the nitro group ($NO_2$ group) of the substituted nitrobenzene compound to a hydroxylamine group (NHOH group).

The inventive transformation described hereinafter are performed in reaction vessels customary for such reactions, the reaction being configurable in a continuous, semicontinuous or batchwise manner. In general, the particular reactions will be performed under atmospheric pressure. The reactions may, however, also be performed under reduced or elevated pressure.

The conversion is effected by hydrogenation of the nitrobenzene compound II preferably in the presence of a solvent.

More preferably, the conversion is effected by reacting the nitrobenzene compound II with hydrazine as reducing agent in the presence of a rhodium catalyst, preferably in a solvent, under suitable reaction conditions.

In the process according to the invention, hydrazine is understood to mean the hydrazine reactant, either as the anhydrous liquid, as hydrazine hydrate comprising about one molecule water per one molecule hydrazine ($N_2H_4 \cdot H_2O$) or as a solution, in particular an aqueous solution, preferably having a water content of 35 to 70% (w/w). Preference is given to using the hydrazine hydrate.

In the rhodium catalyst which is used in the process of the present invention, rhodium is the active metal or makes up at least 80% by weight, in particular at least 90% by weight of the total amount of active metal present in the catalyst. Active metal is the catalytically active metal, i.e. which is involved in the catalytic transfer hydrogenation mechanism.

Apart from rhodium, the catalyst may contain one or more further active metals. These active metals may be present in amounts of up to 20% by weight based on the total amount of active metal, i.e. the total amount of rhodium and further active metal. Further active metal include e.g. group VIIIb metals, group Ib metals and Group VIIb metals of the periodic table (CAS version), such as Pd, Pt, Fe, Co, Ni, Ir, Ru or Cu. Preferably rhodium is the only active metal, i.e. rhodium makes up at least 99% by weight of the active metal present in the catalyst.

The rhodium catalyst used in the present invention may be a full catalyst or a supported catalyst. A full catalyst is a catalyst, where the active metal in its elementary or oxidic form makes up at least 50% by weight in particular at least 80% by weight of the catalyst in its active form. A supported catalyst is a catalyst where the active metal is supported on an inert support material. In a supported catalyst the amount of active metal is principally in the range from 0.05% by weight to 15% by weight, in particular from 0.1 to 10% by weight, more preferably 0.1 to 7% by weight, based on the total amount of active metal and support material. Suitable support materials include active carbon, silicon carbide, silicon dioxide, titanium dioxide, zirconium dioxide, alumina, alumosilicates, such as zeolites. Preferably, the carrier material has a specific surface area, determined by $N_2$ adsorbtion according to DIN 66131 of at least $10\,m^2/g$, in particular from 20 to 1000 $m^2/g$. Preferably the carrier material is selected from the group consisting of silicon dioxide (silica), alumosilicates, alumina, carbon and mixtures thereof. In a particular preferred embodiment, the carrier material comprises at least 90% by weight, based on the weight of the carrier material, of alumina or carbon.

Suitable catalysts are also commercial available (for example from KaiDa Chemicals, Rhorium Carbon, Rhodium alumina; Product Codes 301/302; CAS No's 7440-6)

The catalyst, in particular the supported catalyst, may be in the form of large particles having a particle size 1 to several millimetres, such as moulds, spheres or pellets, or in the form of finely divided particles having an average particle size of below 1000 µm, in particular below 800 µm such as a powder.

Preferably, the rhodium catalyst is used in the form of finely divided particles. The choice of the average particle size of the catalyst depends, however, on several factors, such as the reactivity of the reactants used, whether neat rhodium or supported rhodium is used, and in case of supported rhodium also on the rhodium content of the catalyst as well as the carrier material used. In any event, the appropriate average particle size can be determined by the person skilled in the art in each individual case, for example by simple preliminary tests. The catalyst used in the process of the invention typically has a weight average particle size (weight average) in the range from 10 to 600 µm, preferably in the range from 20 to 200 µm.

It has been proven to be advantageous to activate the catalyst prior to its use in the process of the invention. Activation can be simply achieved by treating the catalyst with hydrogen. Generally, activation can be achieved at temperatures ranging from 0 to 500° C., in particular from 20 to 100° C., e.g. at ambient temperature (i.e. 20 to 30° C.). Activation can be achieved by treatment with pure hydrogen gas or by treatment with a mixture of hydrogen with one or more inert gases. Inert gases include e.g. nitrogen and noble gases such as argon or helium, and mixtures thereof. The partial hydrogen pressure in the gas used for activation will generally be in the range from 0.1 to 20 bar, in particular from 0.2 to 5 bar, e.g. at about 1 bar (0.9 to 1,1 bar). The time required for activation will generally depend from partial hydrogen pressure and activation temperature and will usually require from 10 min to 10 h, in particular from 0.5 to 5 h. Activation can be done immediately prior to the process of the invention. It is, however, also possible to activate the catalyst and to store the activated catalyst under inert atmosphere for a prolonged time period.

The reactants and the catalyst can in principle be contacted with one another in any desired sequence. For example, the rhodium catalyst is added before or after the addition of one of the reactants or else together with one of the reactants, either in the form of a suspension or in bulk If the reduction is carried out using hydrazine, the hydrazine, possibly in dissolved or dispersed form, can be initially charged and admixed with the nitrobenzene compound II as described above. Alternatively, the two reactants, hydrazine and nitrobenze compound can also be added simultaneously to the reaction vessel. The rhodium catalyst is added before or after the addition of one of the reactants or else together with one of the reactants, either in the form of a suspension or in bulk.

It has been found to be appropriate to initially charge the reaction vessel with the nitrobenzene compound II as such, in dispersed form or preferably in dissolved form, then add the rhodium catalyst, as such or in suspended form, and, if hydrazine is used for reduction, subsequently the hydrazine. It is preferred to add the hydrazine gradually over a period of time in order to avoid its accumulation in the reaction mixture. The hydrazine is employed as such or in dissolved form.

Suitable solvents for dissolving or dispersing the reactants are preferably organic solvents that are inert toward the reactants. The choice of the solvent for the conversion in the process of the invention therefore depends on the particular reactants and reaction conditions selected in an individual case. It has generally been found to be advantageous to use an aprotic organic solvent for the conversion of the process of the invention. Useful aprotic organic solvents here include, for example, aliphatic $C_3$-$C_8$-ethers, such as diethyl ether, diisopropyl ether, dibutyl ether, isobutyl methyl ether, methyl tert-butyl ether (MTBE), ethyl tert-butyl ether (ETBE), 1,2-dimethoxyethane (DME) and diethylene glycol dimethyl ether (diglyme), halogenated aliphatic hydrocarbons such as methylene chloride, trichloromethane, dichloroethane and trichloroethane, aliphatic hydrocarbons, such as pentane, hexane, heptane, octane and also petroleum ether, cycloaliphatic hydrocarbons, such as cyclopentane and cyclohexane, alicyclic $C_3$-$C_6$-ethers, such as tetrahydrofuran (THF), tetrahydropyran, 2-methyltetrahydrofuran, 3-methyltetrahydrofuran and 1,4-dioxane, aromatic hydrocarbons, such as benzene, chlorobenzene, anisole, toluene, the xylenes and mesitylene, and mixtures of these solvents with one another.

Preferably the organic solvent for the conversion of the inventive process is selected from aliphatic $C_3$-$C_8$-ethers, such as diisopropyl ether, isobutyl methyl ether, ETBE and methyl tert.-butyl ether MTBE, halogenated aliphatic hydrocarbons, such as methylene chloride, alicyclic $C_3$-$C_6$-ethers, such as tetrahydrofurane (THF) and 1,4-dioxane, and aromatic hydrocarbons, such as chlorobenzene and toluene, and mixtures thereof. More preferably the organic solvent is selected from aliphatic $C_3$-$C_8$-ethers, such as diisopropyl ether, isobutyl methyl ether and MTBE, and alicyclic $C_3$-$C_6$-ethers, such as THF and 1,4-dioxane, and in particular from MTBE and THF. For instance, initially the nitrobenzene compound II may be charged to the reaction vessel solved in an aliphatic ether and after addition of the rhodium catalyst as such or as suspended in an aliphatic ether and, if the reduction is carried out using hydrazine, the hydrazine is added as such or as a solution in an aliphatic or an alicyclic ether.

The total amount of the solvent used in the conversion of the process according to the invention is typically in the range from 200 to 4000 g/mol and preferably in the range from 300 to 3000 g/mol, based in each case on the nitrobenzene compound II.

Preferably the concentration of the nitrobenzene compound II in the total reaction mixture is in the range of 5.0 to 40.0% (w/w), more preferably in the range of 8.0 to 30.0% (w/w), in particular in the range of 10.0 to 30.0% (w/w).

In a preferred embodiment of the invention, the conversion to the N-phenylhydroxylamine I is carried out by employing the hydrogenation agent hydrazine in an amount of 1.0 to 7 mol hydrazine, preferably in an amount of 1.1 to 5.5 mol hydrazine, more preferably in an amount of 2.5 to 4.5 mol hydrazine, in particular in an amount of 3.0 to 4.0 mol hydrazine and specifically in an amount of 3.2 to 3.7 mol hydrazine, in each case relative to 1 mol of the nitrobenzene compound II to be hydrogenated.

In another preferred embodiment of the invention, the conversion to the N-phenylhydroxylamine I is carried out by employing the rhodium catalyst in an amount of $10^{-5}$ to $10^{-2}$ mol rhodium, preferably in an amount of $10^{-4}$ to $10^{-2}$ mol rhodium, in each case based on 1 mol of the substituted nitrobenzene compound.

In general, the conversion of the process according to the invention is performed under temperature control. The transfer hydrogenation reaction is typically effected in a closed or open reaction vessel with stirring apparatus.

The reaction temperature of the conversion depends on several factors, such as the activity of the catalyst or the reactivity of the reactants, and can be determined by the person skilled in the art in the individual case, for example by simple preliminary tests. To avoid over-hydrogenation, a pressure which is from atmospheric pressure to 10 bar gauge pressure is established at the temperature at which the hydrogenation takes place sufficiently rapidly. Usually, the hydrogen gas is introduced into the hydrogenation reactor at atmospheric or slightly superatmospheric pressure. Depending on the solvent used, the reaction temperature and on whether the reaction vessel possesses a vent, a pressure of generally 1 to 5 bar and preferably of 1 to 3 bar is established during the reaction.

If hyradzine Is used for the reduction, the conversion of the process according to the invention is performed under temperature control. The transfer hydrogenation reaction is typically effected in a closed or open reaction vessel with stirring apparatus. The reaction temperature of the conversion depends on several factors, such as the activity of the catalyst or the reactivity of the reactants, and can be determined by the person skilled in the art in the individual case, for example by simple preliminary tests. In general, the conversion is performed at a temperature in the range from −20 to 150° C., preferably in the range from −10 to 100° C., more preferably in the range from −5° C. to 50° C. and specifically in the range from −5° C. to 30° C. Depending on the solvent used, the reaction temperature and on whether the reaction vessel possesses a vent, a pressure of generally 1 to 5 bar and preferably of 1 to 3 bar is established during the reaction.

According to one embodiment of the invention the reaction mixture of the conversion according to the inventive process is adjusted to a temperature within the aforementioned range, particularly within the range mentioned as preferred, only after the addition of the hydrazine to the mixture containing the nitrobenzene compound II and the ruthenium catalyst has been completed, whereas during the addition of the hydrazine the temperature is kept in the range from −30 to 140° C., preferably in the range from −20 to 90° C., more preferably in the range from −10 to 40° C. and specifically in the range from 10 to 20° C.

The work-up of the reaction mixtures obtained in the hydrogenation reaction according to the invention and the isolation of the substituted N-phenylhydroxylamine I are effected in a customary manner, for example by a work-up routine which includes removal of the catalyst from the reaction mixture, e.g. by filtration. Further steps, which might be included in the work-up routine are removal of a possible aqueous layer, aqueous extractive work-up, removal of the solvent, for example under reduced pressure, or a combination of these measures. Generally, substituted N-phenylhydroxylamines I are obtainable in sufficient purity by applying such measures or a combination thereof. Thus, additional purification steps are usually not necessary and often should also be avoided as many hydroxylamines I are rather labile. If desired, however, further purification can be effected by methods commonly used in the art, such as chromatography.

Preferably, for work-up, the catalyst is removed from the reaction mixture step (a), e.g. by filtration, an aqueous layer that possibly has been formed may or may not be removed and after drying and concentrating of the remaining mixture the crude substituted N-phenylhydroxylamine I is obtained. The product thus isolated can subsequently be retained for uses or sent directly to a use, for example use in a further reaction, or be purified further beforehand.

It is a particular benefit of the invention that the catalyst is not or not significantly poisoned during the transfer hydrogenation and hence, the catalyst can be used in one or more subsequent runs, if the reaction is performed batch-wise, i.e. the catalyst can be recycled. Moreover, this particular benefit allows to perform the reaction continuously, because no significant activity loss occurs during transfer hydrogenation.

In case the substituted N-phenylhydroxylamine I is intended to be subjected to a further reaction it is preferably employed as the crude product that is obtained directly after the aforementioned work-up procedure without additional purification. The crude product may contain as impurities unreacted nitrobenzene compound II. However, these impurities, if present, usually do not interfere with subsequent reactions and, in the event they are converted in such reactions at all, lead to reaction products that can be easily removed from the desired product. In the process of the present invention, over reduction to the corresponding aniline does not noticeably occur and hence, the corresponding aniline compound will not be formed in noticeable amounts. Moreover, the process allows to perform the reaction in a manner that the formation of the aniline compound can be reduced to an extent which does not play any role in subsequent reactions.

The nitrobenzene compounds II used as starting compounds in the conversion of the process according to the invention are either known in the art or they can be prepared by analogy to standard methods of organic chemistry, or else can be prepared as follows:

The compound of formula I thus obtained is reacted with an acylating agent yielding compounds of formula III

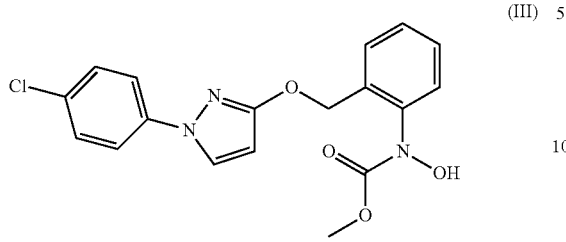
(III)

and reacting compound of formula III thus obtained with an alkylating agent in the presence of a base, to give compound of formula IV

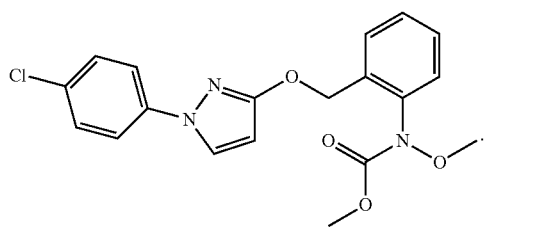
(IV)

These conversions are well known in the art and can be performed in accordance with the methods and conditions as described for example in WO 96/01256 or WO99/12911.

The invention is further illustrated, but not limited by the following examples:

EXAMPLES

Example 1

Method Illustrated by Reduction of Nitro-Compound II

The nitrobenzene compound of formula II (4.12 g, 12.5 mmol) was dissolved in 22.3 g of methyl tert-butyl ether (MTBE). To this solution was added 48 mg (0.01 mmol) of rhodium catalyst (5% rhodium on carbon containing 59% $H_2O$) as a solid. The hydrazine hydrate (2.2 g, 44 mmol) was added to the above stirred mixture over a period of 1 hour while keeping the reaction mixture at ambient temperature. Afterwards the stirring was continued for 1 hour at the same temperature. The reaction progress was monitored by HPLC analysis. The reaction mixture was filtered through a glass frit, which was then washed with 25 mL of MTBE. From the combined filtrates, a water layer, if present, was removed. The organic phase was dried over sodium sulphate and concentrated under reduced pressure. The crude product thus obtained was optionally purified by column chromatography.

Results are summarized in table 1.

Examples 2 to 6

Examples 2 to 6 were conducted according to the reaction conditions described for example 1. Substrates and results are summarized in table 1.

TABLE 1

| | Comparative examples of simple nitrobenzene derivatives | | | | |
|---|---|---|---|---|---|
| | | Post- | HPLC analysis [area %] | | |
| Example | Nitrocompound | reaction Time [h] | Nitro-compound | Hydroxyl-amine | Aniline |
| 1 | nitrobenzene compound of formula II | 1 | 0 | 99.2 | 0.8 |
| 2 | 1-Chloro-2-nitrobenzene | 1 | 0 | 72.9 | 27.1 |
| 3 | 1-Chloro-4-nitrobenzene | 1 | 0 | 52.8 | 47.2 |
| 4 | 3-Nitrotoluene | 1 | 0 | 73.7 | 24.2 |
| 5 | 2,6-Dimethyl-nitrobenzene | 30 | 10.1 | 0 | 89.9 |
| 6 | Ethyl 2-nitrobenzoate | 30 | complete conversion after 30 h, but direct over-reduction to aniline | | |

Table 1 shows the surprisingly high reaction selectivity in combination with high speed of the reduction of the nitro-compound, if compared with substrates with small substituents.

We claim:

1. A process for the preparation of a substituted N-phenyl-hydroxylamine of formula (I)

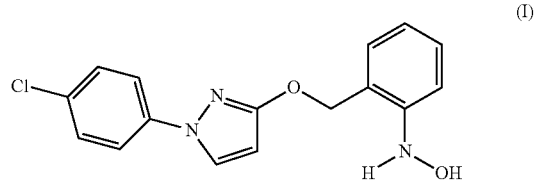 [SMILES: ONc1ccccc1COc1ccn(-c2ccc(Cl)cc2)n1]
(I)

comprising reducing a correspondingly substituted nitrobenzene compound of formula (II),

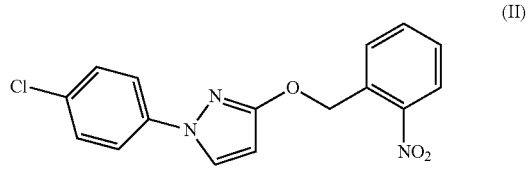 [SMILES: O=[N+]([O-])c1ccccc1COc1ccn(-c2ccc(Cl)cc2)n1]
(II)

wherein the reaction is carried out by reacting the compound of formula (II) with hydrogen or hydrazine in the presence of a rhodium catalyst.

2. The process according to claim 1, wherein the reaction is carried out by reacting the compound of formula (II) with hydrazine in the presence of a rhodium catalyst.

3. The process according to claim 1, wherein the catalyst is a supported catalyst comprising rhodium which is supported on an inert support material.

4. The process as claimed in claim 1, wherein the catalyst has a rhodium content of 0.1 to 10 percent by weight, based on the total weight of the catalyst.

5. The process as claimed in claim 1, wherein the catalyst is employed in an amount of $10^{-5}$ to $10^{-2}$ mol rhodium, based on 1 mol of the compound of formula (II).

6. The process as claimed in claim 1, wherein a catalyst is employed which has been activated by treatment with hydrogen.

7. The process as claimed in claim 1, wherein the reduction is carried out in an aprotic organic solvent.

8. The process as claimed in claim 1, additionally comprising reacting the compound of formula (I) thus obtained with an acylating agent, and reacting compound of formula (III) thus obtained

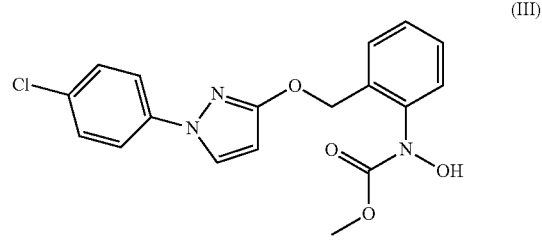 [SMILES: COC(=O)N(O)c1ccccc1COc1ccn(-c2ccc(Cl)cc2)n1]

(III)

with an alkylating agent in the presence of a base, to give compound of formula (IV)

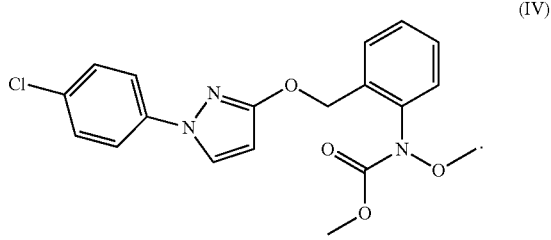 [SMILES: COC(=O)N(OC)c1ccccc1COc1ccn(-c2ccc(Cl)cc2)n1]

(IV)

* * * * *